United States Patent [19]

Boxhoorn et al.

[11] Patent Number: 4,829,044
[45] Date of Patent: May 9, 1989

[54] SILVER CATALYST AND PROCESS FOR ITS PREPARATION

[75] Inventors: Gosse Boxhoorn; Aan H. Klazinga, both of Amsterdam, Netherlands

[73] Assignee: Shell Oil Company, Houston, Tex.

[21] Appl. No.: 115,507

[22] Filed: Nov. 3, 1987

[30] Foreign Application Priority Data

Nov. 7, 1986 [GB] United Kingdom ............... 8626687

[51] Int. Cl.$^4$ ...................... B01J 21/04; B01J 23/04; B01J 23/36; B01J 23/50
[52] U.S. Cl. .................................... 502/348; 549/536
[58] Field of Search ................ 502/347, 348; 549/536

[56] References Cited

U.S. PATENT DOCUMENTS

| | | | |
|---|---|---|---|
| 3,449,078 | 6/1969 | Quik et al. ..................... | 502/347 X |
| 4,341,664 | 7/1982 | Antos ................................. | 502/327 |
| 4,342,667 | 8/1982 | Armstrong et al. ................ | 502/347 |

*Primary Examiner*—W. J. Shine

[57] ABSTRACT

The invention relates to a process for preparing a silver catalyst suitable for use in the oxidation of ethylene to ethylene oxide characterized in that an alkali metal enriched alumina carrier, which has been calcined, is impregnated with a solution of a silver compound, sufficient to cause precipitation on the carrier of from 1 to 25 percent by weight, on the total catalyst, of silver, and before, during or after that impregnation also with one or more dissolved potassium, rubidium or cesium compounds as promoter and with a rhenium compound, and after precipitation the silver compound on the impregnated carrier is reduced to metallic silver.

18 Claims, No Drawings

SILVER CATALYST AND PROCESS FOR ITS PREPARATION

FIELD OF THE INVENTION

The invention relates to a process for preparing a silver catalyst, suitable for use in the oxidation of ethylene to ethylene oxide, to the silver catalyst and to a process for preparing ethylene oxide.

BACKGROUND OF THE INVENTION

Supported silver catalysts have long been used in the conversion of ethylene and oxygen to ethylene oxide. The use of small amounts of the alkali metals, K, Rb and Cs, were noted as useful promoters in supported silver catalysts in U.S. Pat. Nos. 3,962,136, issued June 8, 1976 and 4,010,115, issued Mar. 1, 1977.

U.S. Pat. No. 3,844,981 issued Oct. 29, 1974, U.S. Pat. No. 3,962,285 issued June 8, 1976 and British Patent No. 1,325,715, published Aug. 8, 1973, disclose the use of silver-rhenium ethylene oxide catalysts. In these patents a high surface area silver derivative such as silver oxide is impregnated with a rhenium solution and subsequently reduced to provide metallic rhenium alloyed with the silver. The '285 patent discloses the use of KOH to precipitate $Ag_2O$ from $AgNO_3$. There is no disclosure in the patents of the use of suitable inert supports such as porous refractory supports. U.S. Pat. No. 4,584,921, issued Oct. 22, 1985, discloses the use of rhenium in silver-supported ethylene oxide catalysts. In this reference, the rhenium is first placed on the support in the form of finely divided metal particles and the silver is subsequently deposited on the outer surface of the particles. U.S. Pat. No. 3,316,279, issued Apr. 25, 1967, discloses the use of rhenium compounds, particularly ammonium and alkali metal perrhenate for the oxidation of olefins to olefin oxides. In this reference, however, the rhenium compounds are used, unsupported along with a reaction modifier (cyanides, pyridines or quinolines) in a liquid phase reaction. U.S. Pat. No. 3,972,829, issued Aug. 3, 1976, discloses a method for distributing catalytically active metallic components on supports using an impregnating solution of catalyst precursor compound and an organic thioacid or a mercaptocarboxylic acid. Catalytically active metals include metals of Groups IVA, IB, VIB, VIIB and VIII, including rhenium and which may be in either the oxidized or reduced state. However, promoting amounts of rhenium in combination with silver and promoter amounts of alkali metal on a porous refractory support are not suggested. U.S. Pat. No. 4,459,372, issued July 10, 1984, discloses the use of rhenium metal in combination with a surface metallated (using Ti, Zr, Hf, V, Sb, Pb, Ta, Nb, Ge and/or Si) alumina or silica. U.S. Pat. No. 4,005,049, issued Jan. 25, 1977, teaches the preparation of a silver/transition metal catalyst useful in oxidation reactions. In this instance, the silver serves as both a catalyst and a support for the transition metal cocatalyst. In U.S. Pat. No. 4,536,482, issued Aug. 20, 1985, catalytically active metals such as Ag and Re are co-sputtered along with a co-sputtered support material on a particular support. U.S. Pat. No. 3,449,078, issued June 10, 1969, discloses silver, alkali metal and rhenium, optionally sulfided, deposited on a carrier, preferably an alumina carrier.

Related applications are U.S. Ser. Nos. 926,025, now U.S. Pat. No. 4,766,105, and 926,026 now U.S. Pat. No. 4,761,394, both filed on Oct. 31, 1986 which relate to supported silver catalysts containing alkali metal and rhenium.

Commercial silver catalysts for the preparation of ethylene oxide are sold under the trade name Shell S809, S829 and S839. During application of these catalysts, one has observed that they becomes less stable, which means that the selectivity and the activity of the catalyst become lower and generally it is more economical to replace them by new silver catalysts after some years.

It is the object of the invention to find silver catalysts with improved stability.

Applicant has now found silver catalysts with improved stability.

SUMMARY OF THE INVENTION

The invention relates to a process for preparing a silver catalyst, suitable for use in the oxidation of ethylene to ethylene oxide characterized in that an alkali metal enriched alumina carrier, which has been calcined, is impregnated with a solution of a silver compound, sufficient to cause precipitation on the carrier of from 1 to 25 percent by weight, on the total catalyst, of silver, and before, during or after that impregnation also with one or more dissolved potassium, rubidium or cesium compounds as promoter and with a rhenium compound, and after precipitation the silver compound on the impregnated carrier is reduced to metallic silver. If desired a sulphur compound is impregnated on the carrier.

The invention further relates to an improved silver catalyst, suitable for use in the oxidation of ethylene to ethylene oxide, characterized by
(a) a calcined, alkali metal enriched alumina carrier,
(b) from 1 to 25 percent by weight of metallic silver, based on the weight of the total catalyst,
(c) an alkali metal of the group consisting of potassium, rubidium and cesium, in the form of their oxide or hydroxide in an amount between 10 and 1000 parts by weight per million parts by weight on the total catalyst, as a promoter, and
(d) a rhenium compound.

If desired the improved silver catalyst comprises as an additional component a sulphur compound.

DESCRIPTION OF THE PREFERRED EMBODIMENTS

The carrier used in the inventive process for the preparation of silver catalysts, is an alkali metal enriched alumina carrier, which has been calcined, preferably to a temperature of between 1200° C. and 1700° C. A large part of the calcined material will be alpha-alumina, but the existence of spinels or other configurations can not be excluded, since the calcined material is enriched with alkali metal. Salts or hydroxide of an alkali metal have been mixed with the original alumina. Suitable salts include fluorides, nitrates, chlorides and sulphates. Suitable metals are lithium, sodium, potassium, rubidium and cesium. Preferred compounds are cesium fluoride, cesium chloride, lithium fluoride, lithium nitrate and cesium hydroxide. Preferably the alkali metal compound is mixed with the alumina in such quantity that the atomic ratio of alkali/aluminum is between 0.001 and 0.1. If desired silicon dioxide is additionally mixed with the alumina in such quantity that the atomic ratio of silicon/aluminum is between 0.1 and 0.5. The aluminas may be modifications which by calcination provide alpha-alumina, such as gamma-alumina. Hydrated aluminas may also be suitable, such as boehmite, which latter by calcining via gamma-alumina provides alpha-alumina.

Preferably the carrier is prepared by mixing an aluminum compound and most preferably an alumina with water and alkali metal salt or hydroxide, extruding the obtained mixture to shaped particles and calcining the shaped particles, preferably to a temperature between 1200° C. and 1700° C. The calcination may be carried out in one or more steps, depending on the choice of alumina modification. Generally a sufficient amount of water is added to form a paste suitable for extrusion. The obtained extrudable paste is then extruded and shaped to particles. The shaped particles are heated in order to evaporate the water. The solid particles are then calcined, preferably to a temperature between 1200° C. and 1700° C.

Suitable aluminas are powders of gamma-alumina, alpha-alumina monohydrate, alpha-alumina trihydrate or beta-alumina monohydrate, which powder during calcination are sintered. At the calcination temperature the crystal structure may be modified. The cubic structure of gamma-alumina is converted into the hexagonal structure of alpha-alumina, depending on the amount and nature of the additive used. The catalytically active surface of the enriched alumina may be between 0.1 and 5 $m^2/g$, preferably between 0.2 and 2 $m^2/g$. The shaped alumina parlicles comprise i.a., bars, rings, pellets, tablets and triangles. They are especially suitable in fixed bed applications in ethylene oxide preparation.

In order to prepare a suitable catalyst the calcined, alkali metal enriched alumina carrier is impregnated with a solution of a silver compound sufficient to cause precipitation on the carrier of from 1 to 25 percent by weight, on the total catalyst, of silver, the so impregnated carrier is separated from the solution and the precipitated silver compound is reduced to metallic silver. Hereinafter several detailed methods will be disclosed.

As a promoter is added to the silver solution, one or more of the alkali metals potassium, rubidium and cesium, preferably in the form of their salts or hydroxides. Although the metals potassium, rubidium and cesium in pure metallic form exist, they are in that form not suitable for use. Therefore, they are administered in a solution of their salts or hydroxide. The alumina carrier is impregnated with the promoter before, during and/or after the impregnation of the silver salt has taken place. The promoter may even be brought on the carrier after reduction to metallic silver has taken place. The amount of promoter generally lies between 10 and 1000 parts by weight of potassium, rubidium or cesium metal per million parts by weight of total catalyst. Preferably amounts between 250 and 750 parts by weight are present on the total catalyst. Other alkali metals may be present in addition to the aforementioned alkali metals, K, Rb and Cs.

The alumina carrier is also impregnated with a rhenium compound. This may be done the same time that the promoter is added, before and/or later. The amount of rhenium, calculated as the metal, brought on the alumina carrier is between 100 and 2000 parts by weight per million parts by weight of total catalyst.

Preferably the rhenium compounds used in the preparation of the catalyst according to the invention are rhenium salts, a rhenium oxide or a rhenium sulphide.

As rhenium salts may be mentioned rhenium halides, such as rhenium tetrafluoride, rhenium hexafluoride, rhenium trichloride, rhenium pentachloride, rhenium tribromide, rhenates and perrhenates.

As oxides of rhenium may be mentioned rhenium sesquioxide ($Re_2O_3$) rhenium dioxide ($ReO_2$), rhenium trioxide ($ReO_3$) and rhenium heptoxide ($Re_2O_7$). Of the perrhenates used in the process according to the invention especially ammonium perrhenate is suitable.

As already mentioned hereinbefore with the rhenium compound also a sulfur compound may be used. It is preferred to use a combination of said compounds. The sulfur compound is preferably added in the form of ammonium sulfate, but other sulfur compounds may be used as well, such as sulfonates, thiols, dimethyl sulfoxide, sulfates, sulfites or thiosulfates.

The rhenium compound (calculated as the metal) in the catalyst is preferably used in an amount of between 100 and 2000 parts by weight per million parts by weight of total catalyst. The sulfur is preferably used in equimolar amounts with respect to the rhenium, but somewhat higher and somewhat lower amounts of sulfur are not excluded.

Preferably as a sulfur compound a sulfate is applied; more preferred, ammonium sulfate is applied.

It has been found that sulfate ions are present on the carrier in an amount between 20 and 500 parts by weight per million parts by weight of total catalyst.

Generally the alumina carrier is mixed with a silver salt or a silver salt-complex containing aqueous solution, so that the alumina carrier is impregnated with said aqueous solution, thereafter the impregnated carrier is separated from the aqueous solution, e.g. by filtration and then dried. The thus obtained impregnated alumina carrier is heated to a temperature in the range of from 100° C. to 400° C., during a period sufficient to cause reduction of the silver salt (complex) to metallic silver and to form a layer of finely divided silver, which is bound to the surface of the alumina carrier. A reducing gas or an inert gas may be conducted over the alumina carrier during this heating step.

There are known several methods to add the silver to the alumina carrier. The carrier may be impregnated with an aqueous silver nitrate containing solution, and then dried after which drying step the silver nitrate is reduced with hydrogen or hydrazine. The alumina carrier may also be impregnated with an ammoniacal solution of silver oxalate or silver carbonate, and then dried, after which drying step the silver oxalate or silver carbonate is reduced to metallic silver by heating to e.g., up to 400° C. Specific solutions of silver salts with solubilizing and reducing agents may be employed as well, e.g., combinations of vicinal alkanolamines, alkyldiamines and ammonia.

The amount of promoter generally lies between 10 and 1000 ppm of alkali metal calculated on the total carrier material. Preferably amounts between 250 and 750 ppm are especially suitable. Suitable compounds of potassium, rubidium and cesium are, for example, the nitrates, oxalates, carboxylic acid salts or hydroxides. the most preferred promoter is cesium among the alkali metals, preferably applied in an aqueous solution of cesium hydroxide or cesium nitrate.

There are known excellent methods of applying the promoters coincidentally with the silver on the carrier. Suitable alkali metal salts are generally those which are soluble in the silver-precipitating liquid phase. Besides the above-mentioned compounds may be mentioned the nitrites, chlorides, iodides, bromides, bicarbonates, acetates, tartrates, lactates and isopropoxides. The use of alkali metal salts which react with the silver salt in solution may be avoided, e.g., the use of potassium chloride together with silver nitrate in an aqueous solution, since then silver chloride is prematurely precipitated. The use of potassium nitrate is recommended instead of potassium chloride. However, potassium chloride may be used together with a silver salt-amine-complex in aqueous solution, since then silver chloride is not precipitated prematurely from the solution.

The amount of promoter on the alumina carrier may also be regulated within certain limits by removing, such as by washing out, the surplus of alkali material with, for example, methanol or ethanol. Temperatures, contact times and drying with gases may be regulated. Traces of alcohol in the pores of the carrier may be avoided. Alternatively, high temperature processes can be utilized to remove or inactivate excess promoter.

A preferred process of impregnating the alumina carrier consists of impregnating the carrier with an aqueous solution containing a silver salt of a carboxylic acid, an organic amine, a salt of potassium, rubidium or cesium. A potassium containing silver oxalate solution may be prepared. Silver oxide (slurry in water) is reacted with a mixture of ethylene diamine and oxalic acid, so that an aqueous solution of silver oxalate-ethylene diamine-complex is obtained, to which solution is added a certain amount of potassium compound. Other amines, such as ethanolamine, may be added as well. A potassium containing silver oxalate solution may also be prepared by precipitating silver oxalate from a solution of potassium oxalate and silver nitrate and rinsing with water or alcohol the obtained silver oxalate in order to remove the adhering potassium salt until the desired potassium content is obtained. The potassium containing silver oxalate is then solubilized with ammonia and/or an amine in water. Rubidium and cesium containing solutions may be prepared also in these ways. The impregnated alumina carriers are then heated to a temperature between 100° C. and 400° C., preferably between 125° C. and 325° C.

It is observed that independent of the form in which the silver is present in the solution before precipitation on the carrier, the term "reduction to metallic silver" is used, while in the meantime often decomposition by heating occurs. We prefer to use the term "reduction", since the positively charged Ag+ ion is converted into metallic Ag atom. Reduction times may generally vary from 5 min to 8 hours, depending on the circumstances.

The promoter on the alumina surface is preferably present in the form of an oxide of potassium, rubidium or cesium. Mixtures of oxides are not excluded.

The silver catalysts according to the present invention have been shown to be particularly selective and stable catalysts in the direction oxidation of ethylene with molecular oxygen to ethylene oxide. The conditions for carrying out such an oxidation reaction in the presence of the silver catalysts according to the present invention broadly comprise those already described in the prior art. This applies, for example, to suitable temperatures, pressures, residence times, diluent materials, such as nitrogen, carbon dioxide, steam, argon, methane or other saturated hydrocarbons, presence or absence of moderating agents to control the catalytic action, for example, 1-2-dichloroethane, vinyl chloride or chlorinated polyphenyl compounds, the desirability of employing recycle operations or applying successive conversions in different reactors to increase the yields of ethylene oxide, and any other special conditions which may be selected in processes for preparing ethylene oxide. Pressures in the range of from atmospheric to 35 bar are generally employed. Higher pressures are, however, by no means excluded. Molecular oxygen employed as reactant can be obtained from conventional sources. The suitable oxygen charge may consist essentially of relatively pure oxygen, a concentrated oxygen stream comprising oxygen in major amount with lesser amounts of one or more diluents, such as nitrogen and argon, or another oxygen-containing stream, such as air. It is therefore evident that the use of the present silver catalysts in ethylene oxidation reactions is in no way limited to the use of specific conditions among those which are known to be effective.

In a preferred application of the silver catalysts according to the present invention, ethylene oxide is produced when an oxygen-containing gas is contacted with ethylene in the presence of the present catalysts at a temperature in the range of from 190° C. to 285° C. and preferably 200° C. to 270° C.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

Generally in the reaction of ethylene with oxygen to produce ethylene oxide, the ethylene present is at least a double amount (on a mol basis) compared with the oxygen, but the applied amount of ethylene is often much higher. Therefore, the conversion is calculated according to the mol percentage of oxygen, which has been used. The oxygen conversion is dependent on the reaction temperature, which latter is a measure for the activity of the catalyst employed. The values $T_{30}, T_{40}$ and $T_{50}$ indicate the temperatures at 30 mol. %, 40 mol. % and 50 mol. % conversion of the oxygen respectively in the reactor, and the values T are expressed in °C. These temperatures are higher when the conversion of the oxygen is higher. Moreover these temperatures are strongly dependent on the employed catalyst and reaction conditions. The selectivities (to ethylene oxide) indicate the molar percentage of ethylene oxide in the reaction mixture compared with the total molar amount of converted matter. The selectivity is indicated e.g., as $S_{30}$, $S_{40}$ and $S_{50}$, which means the selectivity at 30, 40 and 50 mol. % oxygen conversion respectively.

The stability of the silver catalyst cannot be expressed directly. To measure the stability experiments during a considerable time, e.g., a year would be necessary. Applicant has now found that these time consuming tests can be simulated by carrying out the experiments during about one month under the extreme high velocities of up to thirty thousand liters gas liter catalyst$^{-1}$h$^{-1}$ (also indicated as GHSV). These velocities are much higher than that used in commercial ethylene oxide processes (the latter GHSV=3300). During the whole test period the above defined S and T values are measured regularly. After the reaction has finished, the total amount of produced ethylene oxide per ml of catalyst is determined. The selectivity and the activity of the catalyst are extrapolated on the basis that one ml of catalyst would have produced 1000 g of ethylene oxide. The new catalyst is considered to be more stable than a standard catalyst, if the differences in T- and S-values, measured on the new catalyst (preferably at the beginning and at the end of the reaction) are smaller than those measured on the standard catalyst, which in every experiment is present. The stability tests are carried out at constant oxygen conversion of 35%.

EXAMPLE

8 Grams of cesium fluoride dissolved in 832 ml water was mixed with 800 g of Kaiser alumina (26405) (Al$_2$O$_3$.H$_2$O) by addition of the cesium fluoride solution of the alumina, and the mixture was kneaded during 30 min. The obtained paste was extruded. The obtained shaped pieces were dried at 120° C. and then calcined at periodically increased temperature. Up to 700° C. was calcined firstly at an increase in temperature of 200° C./h, then was calcined for one hour at 700° C., whereafter the temperature in two hours reached 1600° C. Finally was calcined further for one hour at 1600° C. The pore volume of the alpha-alumina shaped pieces was 0.45 ml/g and the average pore diameter was 1.6 $\mu$m. The obtained ring-shaped pieces were impregnated with an aqueous solution of silver oxalate, to which cesium hydroxide, ammonium perrhenate and ammonium sulphate was added. The impregnation was carried out for 10 min. under vacuum, whereafter the shaped pieces were separated from the aqueous solution, and then placed in a heat air stream at a temperature of 250°-270° C. during 10 min. in order to convert the silver oxalate into metallic silver. The aqueous solution of silver oxalate contained 28 percent by weight of Ag (calculated on the total weight of the solution), wherein the silver oxalate was complexed with ethylene diamine and to which solution had been added cesium hydroxide, ammonium perrhenate and ammonium sulphate. The impregnated shaped pieces before heat treatment contained 17.1 per cent by weight (calculated on the weight of the total catalyst) of silver and 280 ppm of cesium per million parts and 1 micromole of ammonium perrhenate and 1 micromole of ammonium sulphate per gram (of total catalyst). The pieces were subsequently calcined.

A steel cylindric reactor with a length of 15 cm and a diameter of 3 mm was filled completely with catalyst particles of about 0.3 mm. The reactor was placed in a bath, which consisted of silicon/aluminum particles in a fluidized state. A gas mixture with the following composition was conducted through the reactor: 30 mol. % ethylene, 8.5 mol. % oxygen, 7 mol. % carbon dioxide and 54.5 mol. % nitrogen and 7 parts, per million parts of gas, of vinyl chloride as moderator. The GHSV was 10,000 1.1$^{-1}$.h$^{-1}$. The pressure was 15 bar and the temperature was dependent of the oxygen conversion. The measuring instruments were connected to the reactor and to a computer, in such a way that conversion and temperature could be regulated precisely. With the aid of gas chromatography or mass spectroscopy the content of each reaction component was determined. The stability test was carried out at a constant oxygen conversion of 30%. During the test, at regular intervals, the selectivity to ethylene oxide was determined. After 24 days the test was discontinued.

It was found that the selectivity of the catalyst according to the invention after 24 days had decreased 0.1 mol. %, compared with its initial selectivity.

Under the same circumstances the standard catalyst S839 showed a selectivity loss of 0.6- mol. %, after already 18 days of operation. S839 Catalyst contains about 13.5% silver and about 220°-250 ppp alkali metal supported on as alpha alumina carrier.

We claim:

1. A process for preparing a silver catalyst suitable for use in the oxidation of ethylene to ethylene oxide characterized in that an alkali metal enriched alumina carrier, which has been calcined, is impregnated with a solution of a silver compound, sufficient to cause precipitation on the carrier of from 1 to 25 percent by weight, on the total catalyst, of silver, and before, during and/or after that impregnation also with one or more dissolved potassium, rubidium or cesium compounds as promoter and with a rhenium compound, and after precipitation the silver compound on the impregnated carrier is reduced to metallic silver.

2. The process according to claim 1, characterized in that also a sulfur compound is impregnated on the carrier.

3. The process according to claim 1 or 2, characterized in that the alumina carrier is calcined to a temperature of between 1200° C. and 1700° C.

4. The process according to claim 1 or 2, characterized in that the alumina carrier is prepared by mixing an alumina with water and with cesium fluoride, cesium chloride, lithium fluoride, lithium nitrate or cesium hydroxide prior to calcining.

5. The process according to claim 4, characterized in that an alkali metal compound is mixed with the alumina in such quantity that the atomic ratio of alkali/aluminum is between 0.001 and 0.1.

6. The process according to claim 5, characterized in that silicon dioxide is additionally mixed prior to calcining with the alumina in such quantity that the atomic ratio of silicon/aluminum is between 0.1 and 0.5.

7. The process according to claim 1, characterized in that the enriched alumina carrier is extruded and shaped to particles, which are calcined to a temperature of between 1200° C. and 1700° C.

8. The process according to claim 1, characterized in that the promoter is present in an amount between 10 and 1000 parts by weight of potassium, rubidium or cesium metal per million parts by weight of total catalyst.

9. The process according to claim 8, characterized in that the promoter is present in an amount between 250 and 750 parts by weight.

10. The process according to claim 1, characterized in that the rhenium compound is a rhenium salt or a rhenium oxide or sulfide.

11. The process according to claim 10, characterized in that the rhenium salt is a rhenate.

12. The process according to claim 11, characterized in that ammonium perrhenate is used.

13. The process according to any one of claims 2 and 10-12, characterized in that a sulfate is impregnated on the carrier.

14. The process according to claim 13, characterized in the sulfate is ammonium sulfate.

15. The process according to any one of claims 1, 9, 10, or 12 characterized in that the amount of rhenium calculated as a metal, brought on the alumina carrier is between 100 and 2000 parts by weight per million parts by weight of total catalyst.

16. A silver catalyst, suitable for use in the oxidation of ethylene to ethylene oxide, comprising
(a) a calcined, alkali metal enriched alumina carrier, (b) from 1 to 25 percent by weight of metallic silver, based on the weight of the total catalyst,
(c) an alkali metal of the group consisting of potassium, rubidium and cesium and mixtures thereof in the form of an oxide in an amount between 10 and 1000 parts by weight per million parts by weight of the total catalyst as a promoter, and
(d) a rhenium compound.

17. The silver catalyst according to claim 16, characterized in that the amount of rhenium compound present on the carrier is between 100 and 2000 parts by weight per million parts by weight of total catalyst.

18. The silver catalyst according to claim 16 or 17, characterized in that sulfate-ions are also on the carrier in an amount between 20 and 500 parts by weight per million parts by weight of total catalyst.

* * * * *